United States Patent [19]

Inoue

[11] Patent Number: 5,239,365
[45] Date of Patent: Aug. 24, 1993

[54] METHOD OF MEASURING THICKNESS OF LIQUID CRYSTAL CELLS

[75] Inventor: Tomokuni Inoue, Shiga, Japan

[73] Assignee: Otsuka Electronics Co., Ltd., Osaka, Japan

[21] Appl. No.: 858,644

[22] Filed: Mar. 27, 1992

[30] Foreign Application Priority Data

Apr. 3, 1991 [JP] Japan .................. 3-071150

[51] Int. Cl.$^5$ ........................................... G01B 11/06
[52] U.S. Cl. ................................... 356/367; 356/382
[58] Field of Search ................ 356/364, 365, 366, 367, 356/368, 381, 382

[56] References Cited

U.S. PATENT DOCUMENTS

| | | | |
|---|---|---|---|
| 4,269,511 | 5/1981 | Erwin | 356/369 |
| 4,272,195 | 6/1981 | Kaye | 356/368 |
| 4,909,630 | 3/1990 | Gawrisch et al. | 356/364 |
| 5,172,187 | 12/1992 | Brosig | 356/364 |

FOREIGN PATENT DOCUMENTS 2-118406  5/1990  Japan .
2120382  11/1983  United Kingdom .

OTHER PUBLICATIONS

"Optical Properties of General Twisted Nematic Liquid-Crystal Displays" by Hiap Liew Ong Appl. Phys. Lett. 51 (18) pp. 1398-1400, Nov. 2, 1987.

*Primary Examiner*—Richard A. Rosenberger
*Attorney, Agent, or Firm*—Sughrue, Mion, Zinn, Macpeak & Seas

[57] ABSTRACT

A thickness of a liquid crystal cell is measured by placing a liquid crystal cell having a twist angle of $\theta$ between a polarizer and an analyzer, by measuring the strength of transmitted light through the analyzer with the polarizing angle of the polarizer tilted by 45° from the orientation of the liquid crystal cell at its entry surface, and the polarizing angle of the analyzer tilted by further 45° from the orientation of the liquid crystal at its output surface, by calculating retardation $d\Delta n$ from the measured light strength, and by deriving a cell thickness d from both the retardation $d\Delta n$ and a known birefringence $\Delta n$ of the liquid crystal cell. Since this method provides the distribution of thickness data of liquid crystal cells, good quality liquid cells with uniform construction and thus without color shade can be selected.

1 Claim, 2 Drawing Sheets

METHOD OF MEASURING THICKNESS OF LIQUID CRYSTAL CELLS

BACKGROUND OF THE INVENTION

The present invention relates to a method of measuring thickness of liquid crystal cells.

Liquid crystals are used in a variety of display apparatus. When unevenness takes place on the display of liquid crystals, their performance of a display apparatus is deteriorated. One of the causes which contribute to such display unevenness is nonuniformity in thickness of the liquid crystal cells. Attempts have been made to develop methods of accurately measuring the thickness of the liquid crystal cells. For example, Japanese Unexamined Patent Publication 2-118406 has disclosed a method for measuring the thickness of a liquid crystal cell, based on retardation R, between ordinary ray and extraordinary ray, experimentally obtained according to the characteristic that liquid crystals show optical anisotropy. Specifically, interference fringes are generated under crossed-Nicol conditions, and the strength of output light is measured varying the wavelength of the light. Wavelength $\lambda_0$ corresponding to an order number m which produces a maximum or a minimum strength of output light is obtained, and then retardation R is determined by the following equation:

$$R/\lambda 0 = m$$

Further, in the method disclosed, since difference $\Delta n$ between an index of refraction no of the ordinary ray and an index of refraction of ne of the extraordinary ray is a known value, the thickness d according to the retardation R is determined as follows:

$$R = \Delta n \cdot d$$

Although the above-mentioned method can be applied to ordinary optical anisotropic crystals, it cannot be applied to a liquid crystal, such as a twisted nematic liquid crystal (referred to as TN liquid crystal, hereinafter), in which the orientation of the molecules varies spatially.

An equation describing the propagation of light in the TN liquid crystal has been found. Reference is made to H. L. Ong, Appl. Phys. Lett. 51(18), Nov. 2, 1987, pp 1398-1400. Stated in this reference is an equation (equation (3) in the reference), into which the orientation of an analyzer, the orientation of a polarizer, an index of refraction of a liquid crystal, a twist angle, the angle of liquid crystal molecules with respect to a base plate (pre-tilt angle) and a cell thickness are all factored in a generalized manner.

It is an object of the present invention to provide a method of accurate thickness measurement in a TN liquid crystal, by applying the above-mentioned equation which describes the propagation of light in the TN liquid crystal.

SUMMARY OF THE INVENTION

To achieve the above object, the method of thickness measurement in the liquid crystal cells comprises placing a liquid crystal cell having an twist angle of $\theta$ into between a polarizer and an analyzer, measuring the strength of transmitted light through the analyzer with the polarizing angle of the polarizer tilted by 45° from the orientation of the liquid crystal cell at its entry surface, and the polarizing angle of the analyzer tilted by further 45° from the orientation of the liquid crystal at its output surface, calculating retardation $d\Delta n$ from the measured light strength, and deriving a cell thickness d from both the retardation $d\Delta n$ and a known birefringence $\Delta n$ of the liquid crystal cell.

In the above setup, assuming that the wavelength of light is $\lambda$, the refractive index of the TN liquid crystal is no, the extraordinary refractive index of the TN liquid crystal is ne, a pre-tilt angle is 0°, the thickness of the TN liquid crystal is d, the twist angle of the TN liquid crystal is $\theta$, the orientation of the entry surface of the TN liquid crystal is 0°, the polarizing angle of the polarizer is 45°, and the polarizing angle of the analyzer is $(\theta+45°)$, then, the light strength picked up by the analyzer is expressed by the following simple equation, according to the equation (3) of the above quoted reference.

$$\cos^2\{\theta(1+u^2)^{\frac{1}{2}}\}$$

where $$u = \pi d(ne-no)/\theta\lambda$$

An wavelength $\lambda 0$ and an order number $m_0$, resulting in a maximum strength of light, are determined by varying the wavelength $\lambda$ of light. Then, the following equation is obtained.

$$(ne-no)d = \lambda 0(m_0^2 - \theta^2/\pi^2)^{\frac{1}{2}} \quad (1)$$

Since the twist angle $\theta$ of the TN liquid crystal is determined by the orientation of the base board, and (ne−no) is a known value derived from optical characteristics of the liquid crystals, the equation (1) is used to determine the thickness d.

Compared with a prior art method, where the following equation is used, $$(ne-no)d = m_0\lambda o$$

the method according to the present invention is characterized by the equation into which the twist angle $\theta$ of the TN liquid crystal is factored.

In case of a minimum strength of light, the equation (1) is replaced with the following equation.

$$(ne-no)d = \lambda 0(m_0-\frac{1}{2})^2 - \theta^2/\pi^2)^{\frac{1}{2}} \quad (2)$$

As described above, the method of thickness measurement of the liquid crystal cells according to the present invention, allows retardation of the liquid crystal to be derived using the simple equation that takes into account the twist effect of the liquid crystals, thereby making it possible to measure the thickness of a liquid crystal having any twist angle. Thus, the distribution and uniformity of thickness of each liquid crystal cell are properly controlled. This allows liquid crystal cell products to be screened for less uniform ones to be rejected, and thus, provides good quality liquid crystal cells without color shade.

BRIEF DESCRIPTION OF THE DRAWINGS

These and other features, objects, and advantages of the present invention will be more fully apparent from the detailed description set forth below when taken in conjunction with the drawings in which like reference characters identify correspondingly throughout and wherein.

DETAILED DESCRIPTION OF THE PREFERRED EMBODIMENT

Figure 1:
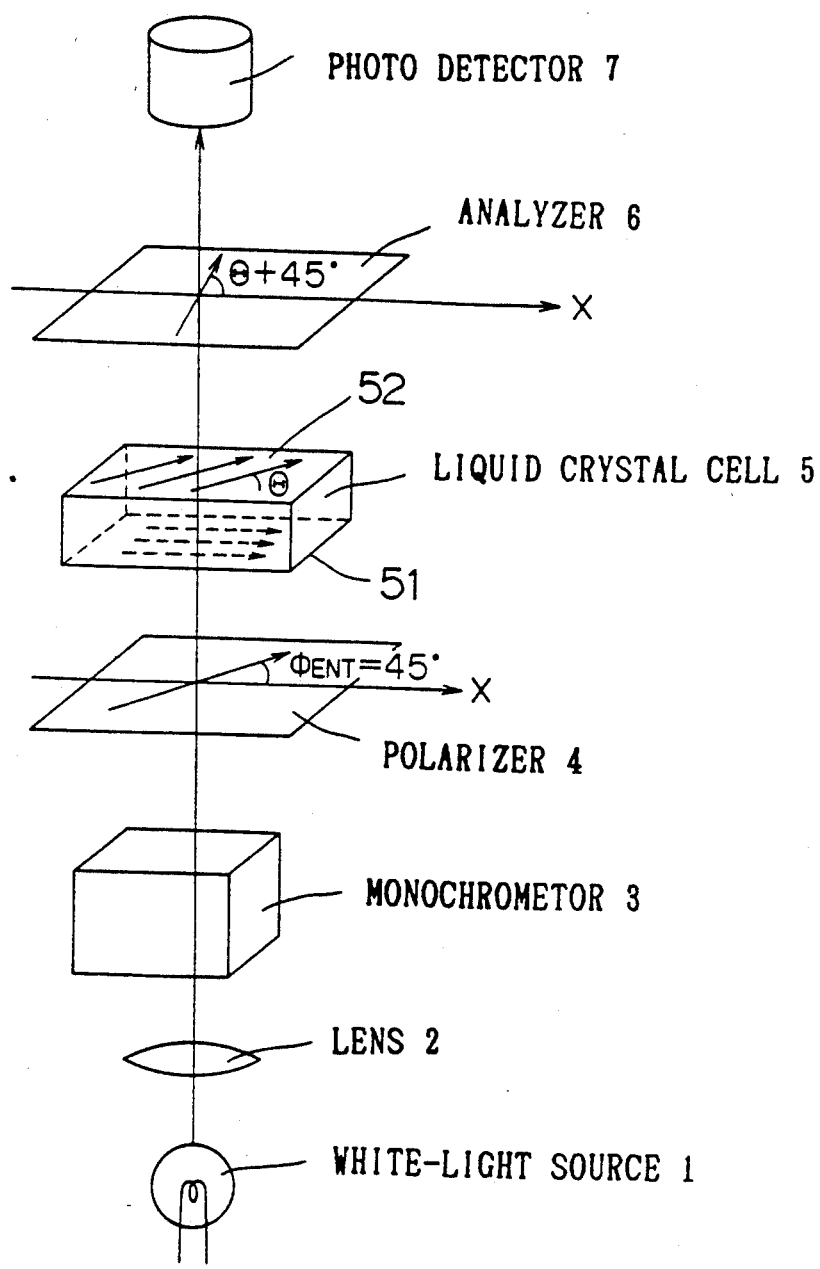
FIG. 1 is a diagrammatic view showing an apparatus which implements the present invention.

FIG. 1 shows a basic configuration of an apparatus which implements the present invention. The basic configuration comprises a white-light source 1, a lens 2 gathering light from the white-light source 1, a monochromator 3 isolating a monochromatic light, a polarizer 4 tilted by 45° relative to the polarization direction (represented by X in FIG. 1) of the incident light, a TN liquid crystal cell 5 having an entry surface 51 of which orientation is equal to the polarization direction of the incident light and having a twist angle of $\theta$, an analyzer 6 of which polarizing direction is tilted by 45° with respect to the orientation of the output surface 52 of the TN liquid crystal cell 5, and a photo detector 7.

The monochromator 3, for example, has concave diffraction grating, with an entry slit disposed along a Rowland circle. The light having a desired wavelength is picked up by moving an output slit along the same Rowland circle.

The polarizer 4 and the analyzer 6 may be a sort of polarizer which makes use of transmission of anisotropic materials such as a Nicol prism, a Glan-Thompson prism, and a linear polarization coating like Lloyd's coating.

The TN liquid crystal cell 5, containing liquid crystal between two glass plates which are connected by spacers, has an angle difference of $\theta$ between the orientation of the entry surface 51 and the orientation of the output surface 52.

The photo detector 7 may be a photoelectric tube, a photoconductive cell, a photodiode, or the like.

Figure 2:
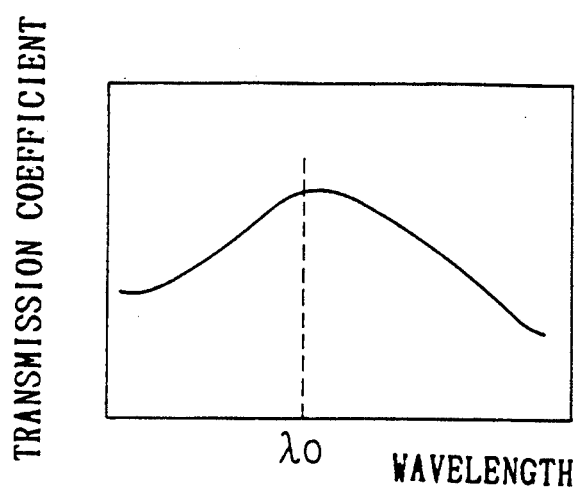
FIG. 2 is a graph illustrating a maximum strength of light.
Figure 3:
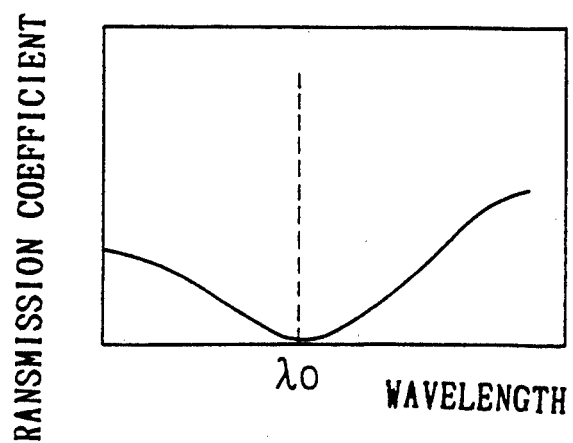
FIG. 3 is a graph illustrating a minimum strength of light.

In the configuration of the embodiment, transmission coefficient varies as shown in FIGS. 2 and 3, when the rotation angle of the monochromator 3 is changed with the white-light source 1 illuminated. When the longest wavelength (order number m=1) giving a maximum transmission coefficient is observed, and that value is substituted in the above equation (1), then, retardation R has the following relation:

$$R = (ne - no)d$$

This equation determines the coating thickness d.

The longest wavelength (order number m=1) giving a minimum transmission coefficient may be observed and then substituted in the equation (2) to determine retardation R and then, the coating thickness d.

To calculate transmission factor in the apparatus in practice, wavelength dependent characteristics of the white-light source 1 and the monochrometer 3 are offset by using reference data which are measured with the TN liquid crystal cell 5 removed and both polarizing angles of the polarizer 4 and the analyzer 6 equalized. Therefore, the thickness color liquid crystal is accurately measured.

Test results may be stored in a computer, and then automatically calculated according to the equations (1) and (2).

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method of thickness measurement of a liquid crystal cell, using a light source, a monochrometer for transmitting only a desired wavelength light in a light beam from said light source, a polarizer for transmitting only a linear-polarized component of the light projected by said monochrometer, an analyzer for transmitting only a linear-polarized component having a fixed orientation, of the light transmitted by the polarizer, and a photo detector for measuring the intensity of the light transmitted through the analyzer and comprising the steps:

placing a liquid crystal cell having a twist angle of $\theta$ into between said polarizer and said analyzer;

tilting the polarizing angle of said polarizer by 45° with respect to the orientation of the light entry surface of said liquid crystal cell;

measuring the strength of light transmitted through said analyzer with the polarizing angle of said analyzer tilted by 45° with respect to the orientation of the light output surface of said liquid crystal cell;

calculating retardation $d\Delta n$ based on the measured light strength; and calculating a thickness of said liquid crystal cell, from said retardation $d\Delta n$ and a known birefringence $\Delta n$ of said liquid crystal cell.

* * * * *